(12) United States Patent
Pinnaduwage et al.

(10) Patent No.: US 7,207,206 B2
(45) Date of Patent: Apr. 24, 2007

(54) CHEMICALLY-FUNCTIONALIZED MICROCANTILEVERS FOR DETECTION OF CHEMICAL, BIOLOGICAL AND EXPLOSIVE MATERIAL

(75) Inventors: Lal A. Pinnaduwage, Knoxville, TN (US); Thomas G. Thundat, Knoxville, TN (US); Gilbert M. Brown, Knoxville, TN (US); John Eric Hawk, Olive Branch, MS (US); Vassil I. Boiadjiev, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 0 days.

(21) Appl. No.: 11/059,170

(22) Filed: Feb. 16, 2005

(65) Prior Publication Data

US 2006/0191320 A1    Aug. 31, 2006

Related U.S. Application Data

(60) Provisional application No. 60/600,762, filed on Aug. 11, 2004, provisional application No. 60/546,072, filed on Feb. 19, 2004.

(51) Int. Cl.
*G01N 7/00* (2006.01)
(52) U.S. Cl. ...................................................... 73/23.2
(58) Field of Classification Search ..................... None
See application file for complete search history.

(56) References Cited

U.S. PATENT DOCUMENTS

| | | | |
|---|---|---|---|
| 5,270,163 A | 12/1993 | Gold et al. | |
| 5,445,008 A | 8/1995 | Wachter et al. | |
| 5,485,096 A | 1/1996 | Aksu | |
| 5,923,421 A | * | 7/1999 | Rajic et al. ................. 356/328 |
| 6,090,269 A | | 7/2000 | Mandler et al. |
| 6,575,020 B1 | | 6/2003 | de Charmoy Grey et al. |
| 6,617,040 B2 | | 9/2003 | Houser et al. |
| 2002/0072127 A1 | * | 6/2002 | Sofield et al. ............... 436/518 |
| 2003/0069002 A1 | * | 4/2003 | Hunter et al. ................ 455/404 |
| 2003/0085348 A1 | | 5/2003 | Megerle |
| 2003/0087301 A1 | | 5/2003 | Smith et al. |
| 2003/0166039 A1 | * | 9/2003 | Hubler et al. .................. 435/34 |
| 2004/0007051 A1 | * | 1/2004 | Bashir et al. ............... 73/61.62 |
| 2004/0038426 A1 | * | 2/2004 | Manalis ...................... 436/514 |
| 2004/0115711 A1 | * | 6/2004 | Su et al. .......................... 435/6 |
| 2004/0152211 A1 | * | 8/2004 | Majumdar et al. .......... 436/518 |
| 2005/0011256 A1 | * | 1/2005 | Hoh ............................. 73/105 |

FOREIGN PATENT DOCUMENTS

| | | |
|---|---|---|
| WO | WO 03/067248 | 8/2002 |
| WO | WO 03/044530 | 5/2003 |
| WO | WO 03/062135 | 7/2003 |

(Continued)

OTHER PUBLICATIONS

L.A. Pinnaduwage, et al., "Sensitive detection of plastic explosives with self-assembled monolayer-coated . . . ," Applied Physics Letters, 2003, pp. 1471-1473, vol. 83, Num. 7.

(Continued)

*Primary Examiner*—Robert Raevis
(74) *Attorney, Agent, or Firm*—Kirk A. Wilson

(57) ABSTRACT

A chemically functionalized cantilever system has a cantilever coated on one side thereof with a reagent or biological species which binds to an analyte. The system is of particular value when the analyte is a toxic chemical biological warfare agent or an explosive.

6 Claims, 5 Drawing Sheets

FOREIGN PATENT DOCUMENTS

| WO | WO 03/071258 | 8/2003 |
| --- | --- | --- |
| WO | WO 03/104784 | 12/2003 |
| WO | WO 2004/059306 | 7/2004 |

OTHER PUBLICATIONS

R.M. Crooks and A.J. Ricco, "New Organic Materials Suitable for Use in Chemical Sensor Arrays," Acc. Chem. Res., 1998, pp. 219-227, vol. 31.

C.Z. Chen and S.L. Cooper, "Interactions between dendrimer biocides and bacerial membranes," Biomaterials, 2002, pp. 3359-3368, vol. 23.

K.J. Albert, et al., "Cross-Reactive Chemical Sensor Arrays," Che. Rev., 2000, pp. 2595-2626, vol. 100.

L.A. Pinnaduwage, et al., "Detection of Hexavalent Chromium in Ground Water Using a single Microcantilever Sensor," Sensor Letters, 2004, pp. 1-6, vol. 2.

Y.M. Yang, et al., "Nerve Agents Detection Using a $Cu^{2+}$/L-Cysteine Bilayer-Coated Microcantilever," J of Am Chem Soc, 2003, pp. 1124-1125, vol. 125.

J.M. Buriak, "Organiometallic Chemistry on Silicon and Germanium Surfaces," Chemical Reviews, 2002, pp. 1271-1308, vol. 102, No. 5.

S. Edmondson, et al., "Polymer brushes via surface-initiated polymerizations," Chem. Soc. rev., 2004, pp. 14-22, vol. 33.

Sumedha D. Jayasena, "Aptamers: An Emerging Class of Molecules that Rival Antibodies in Diagnostics," Clinical Chem, 1999, pp. 1628-1650, vol. 45, Issue 9.

K. Yano and I. Karube, "Molecularly imprinted polymers for biosensor applications," Trends in Analytical Chemistriy, 1999, pp. 199-204, vol. 18, No. 3.

V.I. Boiadjiev, et al., "Photochemical Hydrosilylation f 11-Undecenyltriethylammonium Bromide . . . ," Am. Chem. Soc., 2004.

* cited by examiner

CHEMICALLY-FUNCTIONALIZED MICROCANTILEVERS FOR DETECTION OF CHEMICAL, BIOLOGICAL AND EXPLOSIVE MATERIAL

CROSS-REFERENCE TO RELATED APPLICATIONS

This application claims priority to U.S. Provisional Patent Applications 60/546,072 filed Feb. 19, 2004 and 60/600,762 filed Aug. 11, 2004, both herein incorporated by reference.

STATEMENT REGARDING FEDERALLY SPONSORED RESEARCH

This invention was made with United States Government support under Contract No. DE-AC05-00OR22725 between the United States Department of Energy and U.T. Battelle, LLC. The United States Government has certain rights in this invention.

FIELD OF THE INVENTION

This invention relates to highly sensitive single sensor platforms for the detection of chemical, biological and explosive material using mirocantilevers whose surfaces have been modified with oligomers, polymers, self-assembled monolayers, mixed monolayers, bilayers, and dendrimers of suitable binding coating material. The devices may be used in production facilities, airports, train stations and public buildings to detect poisons, toxins, biological warfare agents and explosives which may be released or introduced into the space. The devices may be fixed or mobile, attended or-unattended, and are intended to be integrated into systems for protection against terrorists and systems malfunctions.

BACKGROUND OF THE INVENTION

The earliest attempts to detect poisons probably entailed animal and human tasters. Nero was able to poison Britannicus by putting arsenic in water which Britannicus used to cool the hot soup which passed his taster's test. The miner's canary long has been used to identify methane gas in mines. Color tests using treated filter paper, impregnated gels and bubblers are useful for many chemicals but have limited utility when looking for biological species or small trace markers for explosives. Likewise for battery powered "monitors" for explosive gas, phosgene and oxygen which have comparatively high lower limits of detection.

U.S. Published Patent Application 2003/0085348 A1 illustrates the difficulties in securing areas. The apparatus includes a room, an air handling system, an ion mobility spectrometer, a surface acoustic wave (SAW) device and ultraviolet fluorescence spectrometer, a Raman spectrometer, a DNA "sensor" with in-situ PCA amplification capability, microIR laser induced visible light, fluoroscope, a flow cytometer having a dye-containing binding agent-covered capsule with reporter bead chemistry and a metal detector. The apparatus requires the presence of an operator.

Cantion A/S is owner of published international applications WO 03104784, WO 03071258, WO 03067248, WO 03062135, WO 03044530, WO 2004059306 and U.S. Pat. No. 6,575,020 which are directed to systems for detection of bio-components in liquid using coated cantilevers with reference cantilevers and in arrays with specific binding partners.

A continuing need exists for simple, reliable and inexpensive detectors for toxic chemicals and biological agents.

BRIEF DESCRIPTION OF THE INVENTION

The invention relates to functionalized cantilever sensors for the detection of toxins, infectious agents, chemical warfare agents and explosives.

It is a first objective of this invention to provide cantilevers specific for toxins such as ricin, Shiga toxin, diphtheria toxin, plague, botulinum toxin, aflatoxin and other toxins derived from molds and plant sources.

It is a second objective of this invention to provide cantilevers specific for the detection of infectious spores such as anthrax.

It is a third objective of this invention to provide cantilevers specific for chemical warfare agents including but not limited to organophosphate and carbamate reagents, blistering agents and components of binary agents.

It is a fourth objective of this invention to provide cantilevers specific for the detection of explosives, especially plastic explosives in luggage, shoes, briefcases, shipped packages and shipping containers.

These and other objectives can be achieved by providing cantilevers functionalized with highly specific binding coatings which bend as the result of changed surface stresses in the presence of ppb amounts of agent.

DETAILED DESCRIPTION OF THE INVENTION

The automated detection of hazardous materials has been of concern for many years, but concern has been heightened as terrorist threats have become a global concern. Small, reliable sensors, passive preferred, are in great demand.

Figure 1A:
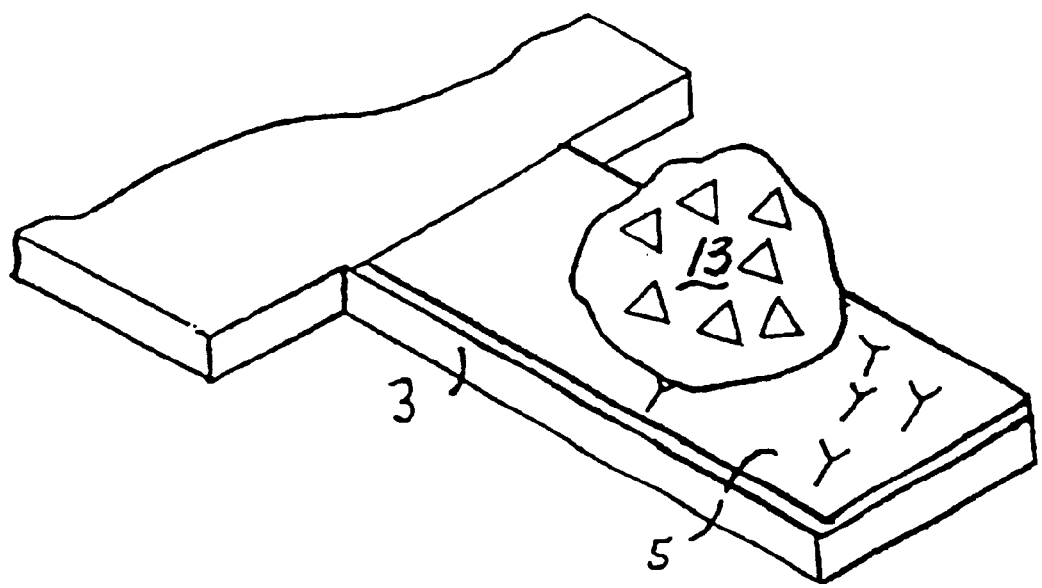
FIGS. 1a and 1b are a schematic representation of a functionalized cantilever.
Figure 1B:
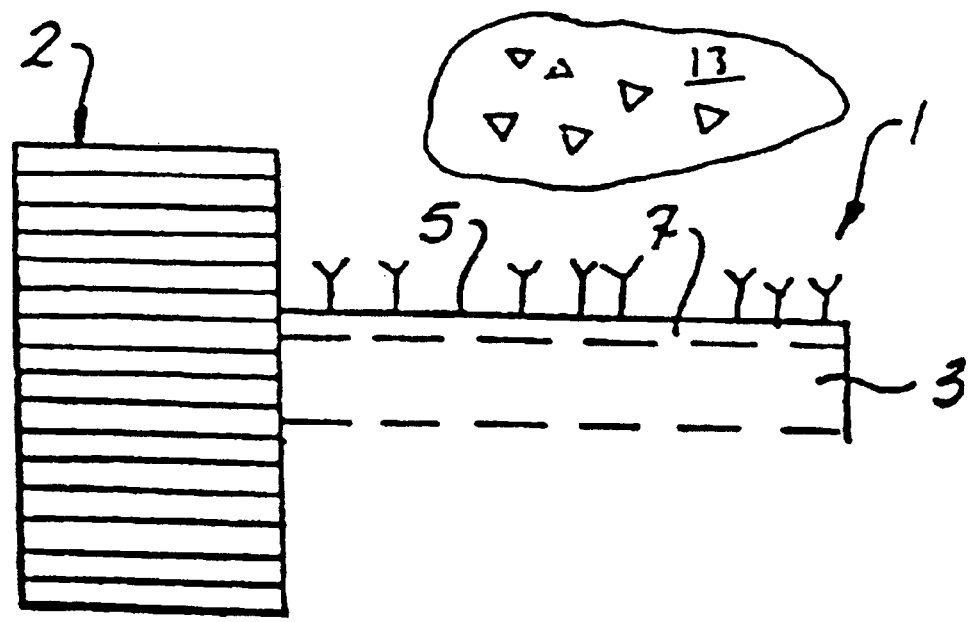

We have discovered that microcantilevers, such as those described in Wachter et al., U.S. Pat. No. 5,445,008 can be functionalized with coatings specific for hazardous compounds and for trace components which are unavoidable contaminants in hazardous compounds. FIG. 1 is a schematic diagram of a cantilever coated with a material responsive to the attachment. Sensor 1 has a base 2, a cantilever 3 coated on surface 5 with an agent specific for analyte 13. Equally important is the capability to identify and quantify a hazardous compound in situ because sample collection and preparation for analyses consume time and money and increase the disparity in costs between terrorism and protection.

The main feature distinguishing microcantilevers from other sensors is their unique bending response. Microcantilevers have a high surface-to-volume ratio ($\approx 10^3$), and therefore changes in the Gibbs surface free energy induced by surface-analyte interactions lead to large surface forces; if such interactions are restricted to one surface, then the resulting differential stress leads to bending of the cantilever. Because of its small size, the cantilever undergoes thermal vibrations, and the resonance frequency of the cantilever can also be detected by feeding the bending signal to a spectrum analyzer (for mass loading measurements). Microcantilevers have dimensions in the 100 micrometer range. The sensitivity of a microcantilever sensor can be increased by decreasing its dimensions. Nanocantilevers typically have a length of approximately 1 micrometer with thickness and width adjusted to be free from size-induced deformations. Unless otherwise specified, the terms cantilever, microcantilever and nanocantilever are used herein interchangeably.

The key to using microcantilevers for selective detection of vapors is the ability to functionalize one surface of the silicon microcantilever so that a given molecular species will be preferentially bound to that surface upon exposure of the cantilever to a vapor stream. Therefore, the sensitivity of detection can be vastly enhanced by applying an appropriate binding coating to one cantilever surface. Another important requirement for a sensor system is fast recovery (sensor reversibility), so that the sensor can be used repetitively.

Of the common explosives that have been used in terrorist bombings, high explosives such as pentaerythritol tetranitrate (PETN) and hexahydro-1,3,5-triazine (RDX), frequently used with plastic filler, are the most serious threats in aircraft sabotage because they can be easily molded for concealment, are very stable in the absence of a detonator, and are able in small amounts to destroy a large airplane, cars, trucks and train cars. They are, in fact, the explosives most commonly used for these purposes. The vapor pressures of PETN and RDX are quite low, in the range of parts per trillion (ppt) at ambient temperatures.

Other hazardous materials which may be screened for are listed in the following table:

| Agent | Medium | Coating |
| --- | --- | --- |
| DNT, TNT | Air | SXFA (fluoroalcohol polysiloxane polymer) |
| DMMP (0-P) | Liquid | $Cu^{2+}$/L-Cys on Arc |
| Ricin | Liquid | Ricin Antibody |
| Staphylococcal enterotixin B | Air/Liquid | Aptamers of the SELEX method |

Commercially available V-shaped silicon cantilevers 180 µm long, 25 µm wide, and 1 µm thick (Park Scientific Instruments, Inc.) were used to determine sensitivity of 4-MBA self assembled monolayers (SAMS). The force constant was 0.26 N/m (manufacturer's specifications). The manufacturer had coated one side of these cantilevers with metallic gold (a 30-nm thick gold layer on top of a 3-nm titanium adhesion layer), and this side was used to reflect the laser beam for deflection measurements. The metallic coating can be selected from at least one of the group consisting of Au, Pt, Cu, Pd, Ti, and their oxides. These metallic/oxide coatings can be used for the detection of chemical species as described below.

Silicon cantilevers were cleaned in acetone, in absolute ethanol, in deionized water, and (for only 10 s) in piranha solution (7:3 $H_2SO_4$ 98%/$H_2O_2$ 31%), and then rinsed with ultra pure deionized water (3 times) and absolute ethanol (2 times). The clean cantilevers were dried briefly in an oven at 80° C. in ambient air. The formation of a 4-MBA SAM on the gold surface of the cantilever was achieved by immersing the cantilever into a $6 \times 10^{-3}$ M solution of 4-MBA (97%, from Aldrich Chemical Company) in absolute ethanol for two days. Upon removal from the solution, the cantilever was rinsed three times with ethanol and then dried before use in the experiments. The monolayer coating was shown to be quite stable for several months under normal operating conditions.

Figure 2:
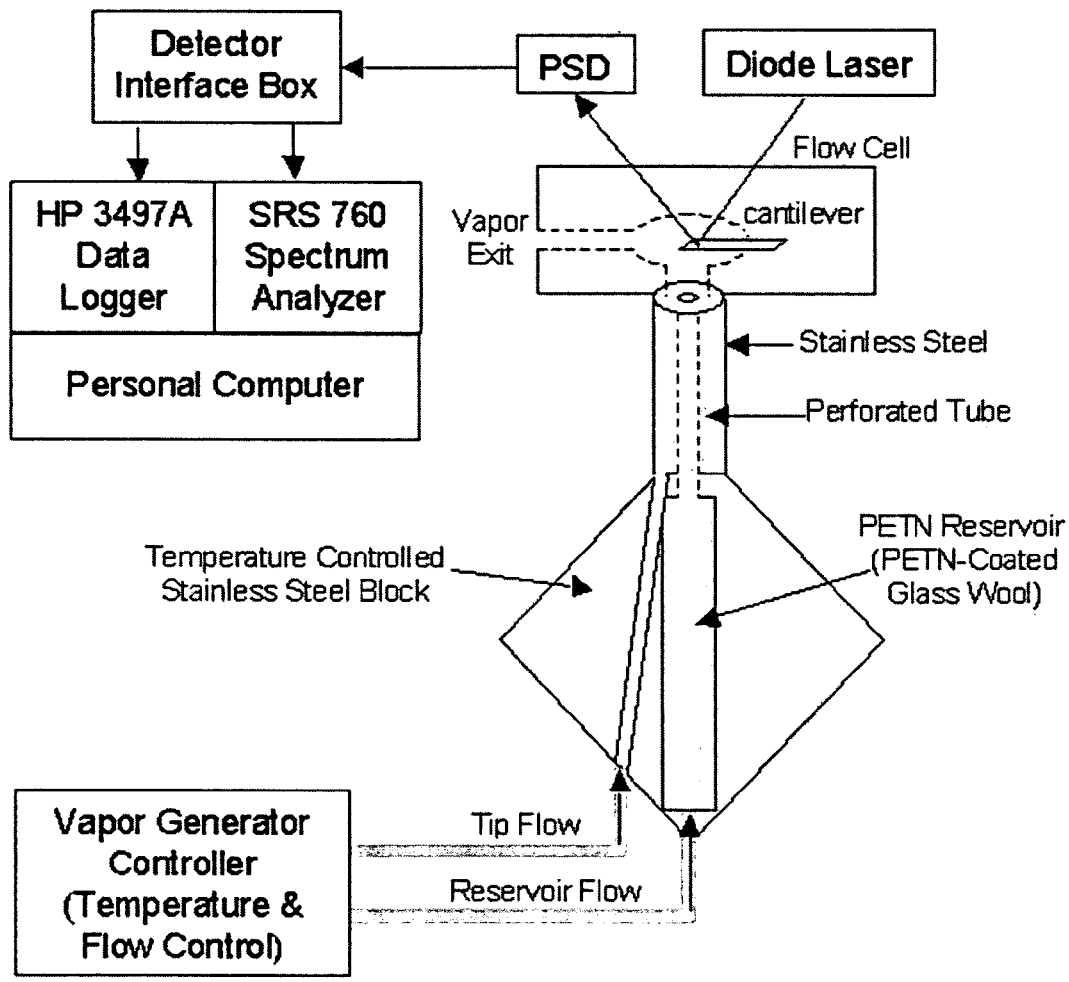
FIG. 2 is a schematic diagram of an experimental apparatus using a PETN vapor generator.

The experimental apparatus used in the present experiments is shown in FIG. 2. The microcantilever was held in place in a vacuum-tight glass flow cell by a spring-loaded wire. A modified atomic force microscope head measured the bending response of the microcantilever. The light from a laser diode was focused at the apex of the cantilever (the gold-coated side on which the monolayer was deposited). The reflected laser beam was allowed to fall on a position-sensitive detector (PSD). The output from the PSD was amplified and normalized through a homemade electronics box and fed to a Stanford Research System model SR 760 FFT spectrum analyzer (for resonance frequency measurements) and a Hewlett Packard model 34970A data logger (for bending measurements). This allowed simultaneous measurement of bending and resonance frequency. The flow rate of gas around the cantilever was kept constant to minimize bending due to gas flow.

A vapor generator developed at Idaho National Engineering and Environmental Laboratory (INEEL) was used to generate the PETN and RDX vapor streams. The vapor stream was generated by flowing ambient air through a reservoir containing PETN or RDX. The reservoir consisted of 0.1 g of PETN or RDX dissolved in acetone and deposited on glass wool contained in a stainless steel block. The reservoir temperature was controlled via thermoelectric elements that cooled or heated the reservoir, generating a level of vapor saturation within the reservoir. When the explosive vapor stream was turned off, the same carrier stream was redirected to bypass the reservoir and was sent through the cantilever flow cell; i.e., the total flow rate through the cantilever flow cell was kept constant. This was done in order to avoid any potential cantilever response to the change of flow. Thus the cantilever was always subjected to a stream of ambient air, in this case at a flow rate of 100 standard cubic centimeters per minute (sccm). Both vapor generators were operated at 50° C. At this temperature, the vapor concentrations for PETN and RDX were 1400 ppt and 290 ppt, respectively.

Figure 3:
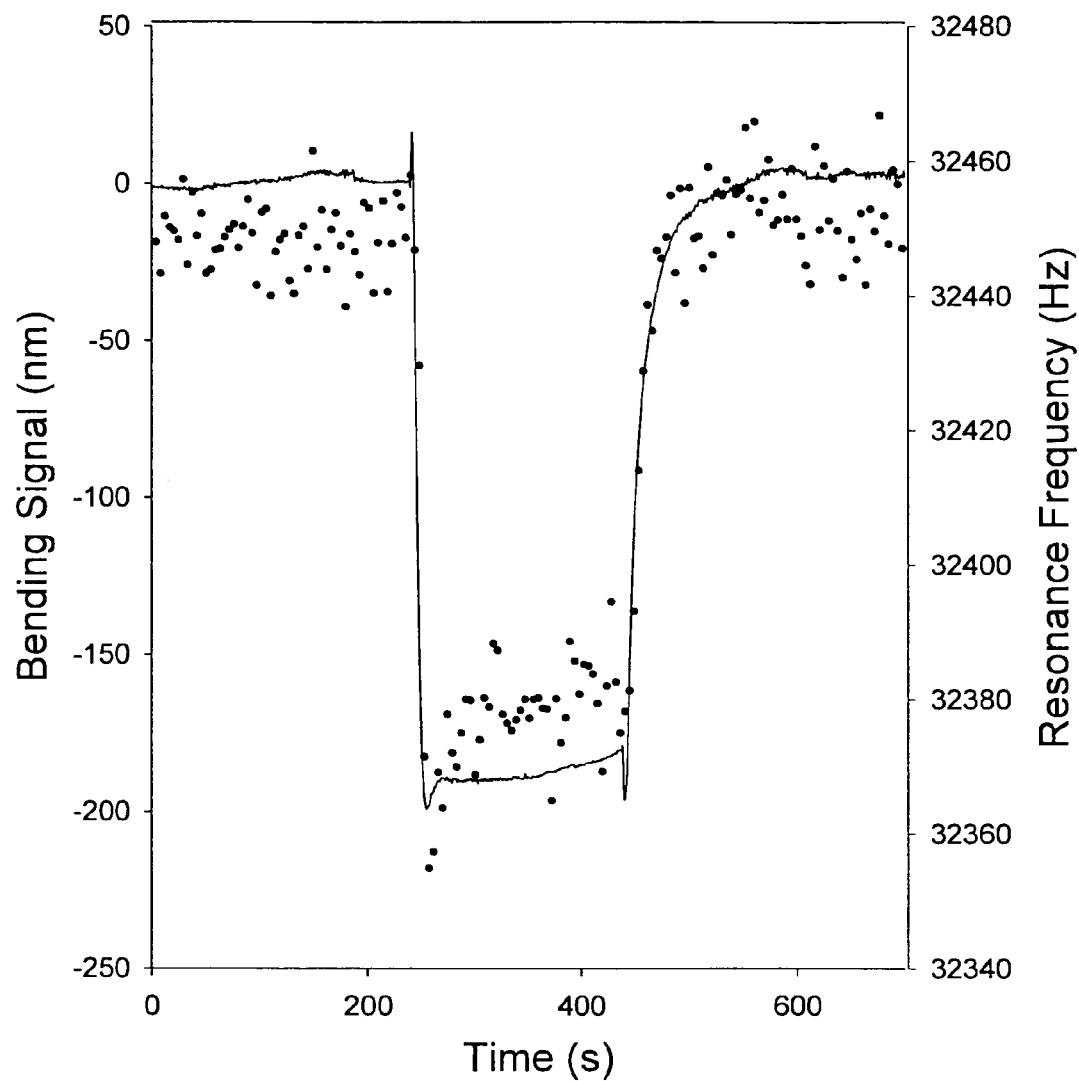
FIG. 3 is the response of a 4-mercaptobenzoic acid (4-MBA)-coated silicon cantilever to a PETN stream of 1.4 ppb concentration in ambient air. The solid curve depicts the bending response, and the dots depict the resonance frequency of the cantilever. The frequency shift due to the adsorption of PETN vapor corresponds to a mass loading of 15 picograms on the cantilever.

The response of a SAM-coated cantilever to a 200-s-long pulse of PETN vapor is shown in FIG. 3. As seen from FIG. 3, the bending response of the cantilever to the PETN exposure is extremely sensitive and fast. Since the noise level of the bending response in these experiments is ≈2 nm (3×standard deviation of the noise level), the detection sensitivity corresponding to FIG. 2 is ≈14 ppt. Maximum bending of the cantilever is achieved within 20 s. The amount of PETN delivered by the generator in 20 s is ≈660 pg. However, the mass of PETN exposed to the cantilever is much smaller, since the cross-sectional area of the hole in the delivery tube of the vapor generator is ≈0.07 cm² and the cantilever surface area is ≈8×10⁻⁵ cm². Allowing for several wall bounces, it can be estimated that a few picograms of PETN impinging on the cantilever in 20 s is sufficient to yield a 200-nm deflection of the cantilever. Since the minimum detection level above the noise level is a few nanometers, a low-femtogram (10⁻¹⁵ g) level of detection (LOD) is implied. It should be noted that with the availability of vapor preconcentrators, the detection capabilities of a given sensor are better described by LOD (based on the amount of explosive material) than by vapor concentration.

Figure 4:
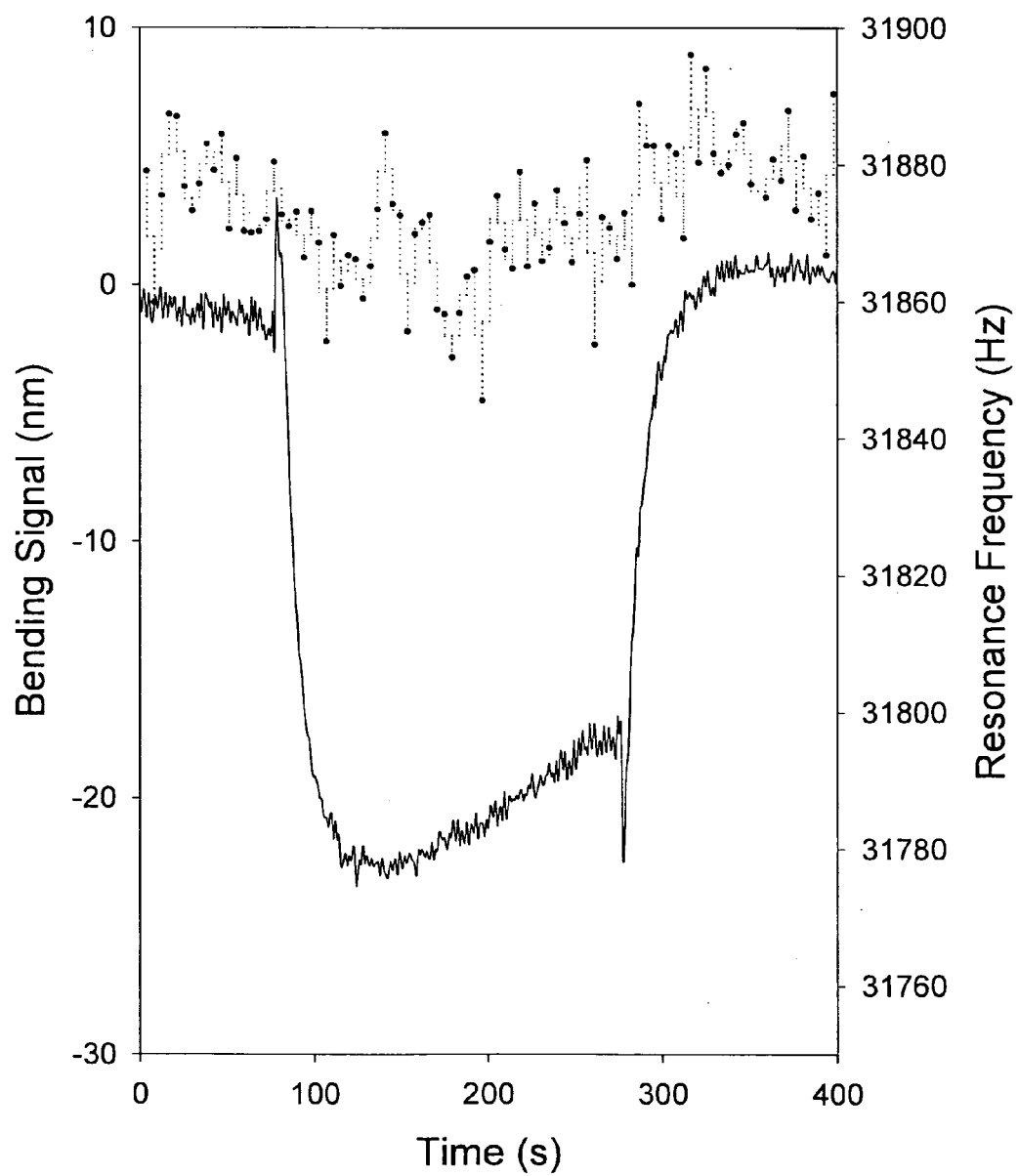
FIG. 4 is the response of a 4-mercaptobenzoic acid (4-MBA)-coated silicon cantilever to a RDX stream of 290 ppt concentration in ambient air. The solid curve depicts the bending response, and the dots depict the resonance frequency of the cantilever. The frequency shift due to the adsorption of RDX vapor is barely discernible.

The bending and frequency responses of the SAM-coated cantilever to an RDX vapor stream with a concentration of 290 ppt are shown in FIG. 4. In this case the frequency response, and thus the mass loading, is quite small. Yet the bending response is quite clear, with a "direct" detection sensitivity of ≈30 ppt. The maximum cantilever bending is achieved within ≈25 s, and the mass of RDX delivered by the generator during this time is ≈96 pg. Again, if we compare the cantilever cross-sectional area with that of the vapor generator, this corresponds to ≈0.1 pg delivered to the cantilever, for a total cantilever deflection of 20 nm (FIG. 2), and thus an implied LOD of a few femtograms.

Figure 5:
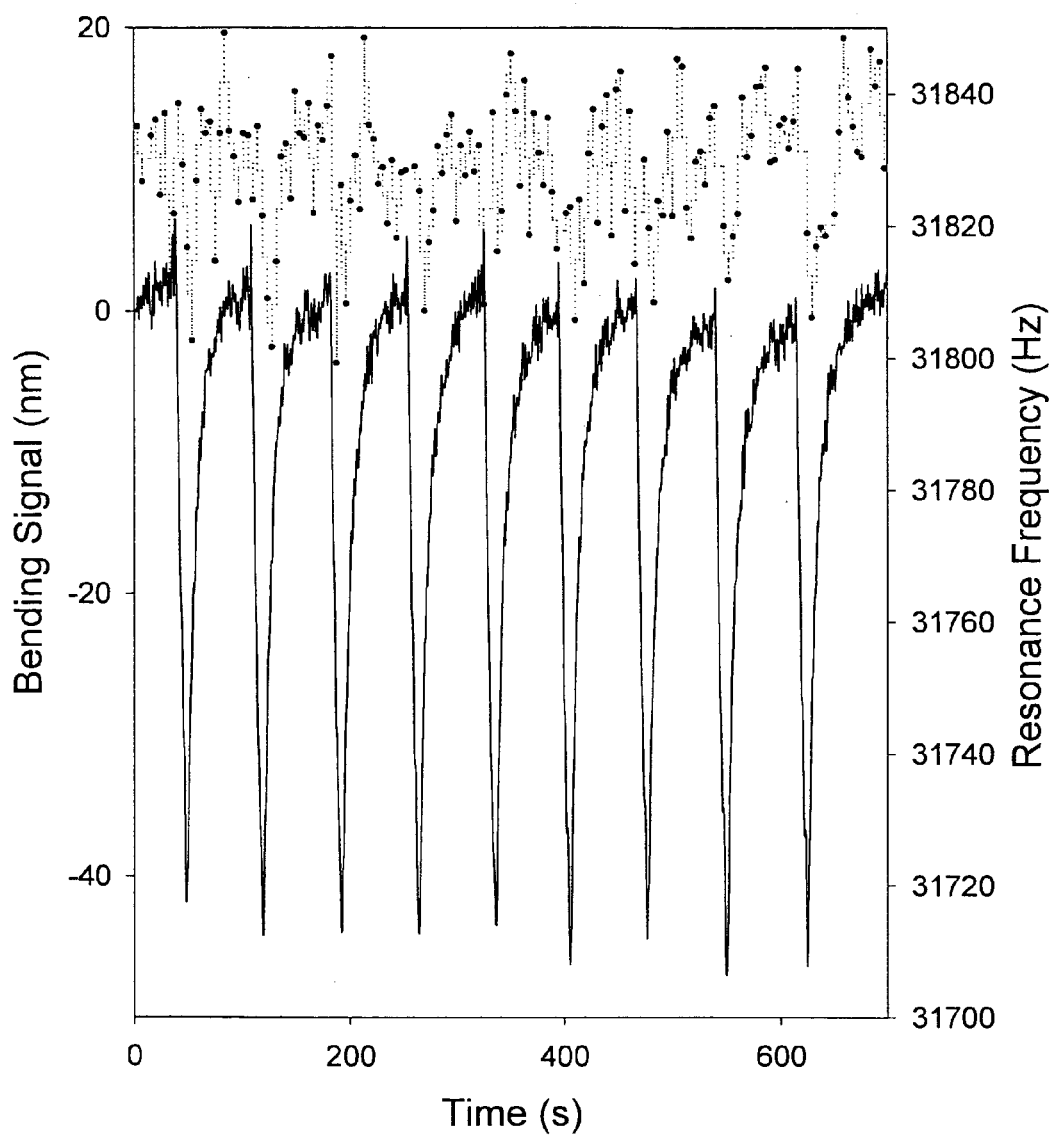
FIG. 5 is the response of a 4-mercaptobenzoic acid (4-MBA)-coated silicon cantilever to the periodic turning on (10 s) and off (60 s) of a PETN stream of 1.4 ppb concentration in ambient air. The solid curve depicts the bending response, and the dots connected by dashed lines depict the resonance frequency of the cantilever.

The rapidity with which explosive vapors can be detected and the relatively fast relaxation of the cantilever when the vapor stream is turned off can be seen in FIG. 5. When the PETN stream is turned on for 10 s, a 40-nm deflection signal is observed; after the vapor stream is turned off, the cantilever is relaxed back almost to the original position within 60 s. Another important observation from the data shown in FIG. 4 is that the resonance frequency of the cantilever does not change significantly as a result of the small amount of PETN deposited in 10 s. The bending of the cantilever is still quite easily detected.

While not bound by any theory, it is thought that the hydrogen bonding between the nitro groups of the explosives molecules and the carboxyl group of 4-MBA is responsible for the easily reversible adsorption of explosive vapors on the SAM-coated top surface of the cantilever. This leads to strong surface stress on the top surface, making the cantilever bend downward, as shown by the data in FIGS. 3–5.

The reversibility of the binding means that the detector can scan areas for "hot spots" indicating the location of explosives and can be used in a pass-through detector such as a baggage screening line at travel departure locations and mail rooms. With the improved level of detection of this device, explosives can be detected further away from their source where the airborne concentration is smaller. This feature allows higher volume throughput and bulk inspection of goods.

The binding of PETN to 4-MBA is reversible, so the detector can be used repeatedly. Binding with very high specificity, such as in antigen antibody reactions effectively contaminates the cantilever permanently and the detector becomes a single use or disposable detector. A replaceable cantilever may be used in such a system. Very high sensitivity has been reported for nucleic acid pouches prepared using the Systematic Evolution of Ligands by Exponential Enrichment (SELX) disclosed in U.S. Pat. Nos. 5,485,096 and 5,270,163 and U.S. Published Patent Application 20030087301.

The other signal transduction method, i.e., the bending response, is unique to the MEMS and NEMS- if a differential surface stress is achieved, for example, by using a coating on one of its broad surfaces, the microcantilever will bend. Since a differential surface stress is required for bending, only one broad surface should be coated for bending mode operation. Therefore, the mass-loading information is used only as a bonus. In the bending mode, microcantilever detection sensitivity is at least an order of magnitude greater than other miniature sensors such as SAW and QCM that are also being investigated as chemical sensors.

It must be emphasized that the bending of the microcantilever is not due to the weight of the deposited material. A 40-ng microcantilever bends about 1 nm due to its own weight, which is just above the noise level for cantilever-bending signal. Therefore, the microcantilever bending due to the weight of the deposited material of pico-gram levels is insignificant. On the other hand, for micron-size objects like microcantilevers, the surface-to-volume ratio is large and the surface effects are enormously magnified. Thus adsorption-induced surface forces can be extremely large. The adsorption-induced force can be viewed as due to change in surface free energy due to adsorption. Free energy density (mJ/m²) is the same as surface stress (N/m). This surface stress is analogous to surface tension in a liquid. Incidentally, surface stress has the units of a spring constant of a cantilever. Therefore, if the surface free-energy density change is comparable to the spring constant of a cantilever, the cantilever will bend. When probe molecules bind to their targets, steric hindrance and electrostatic repulsions cause the bound complexes to move apart. Because they are tethered at one end and because the surface area is finite, they exert a force on the surface. Smaller cantilevers such as NEMS devices are more sensitive.

Another advantage of the MEMS/NEMS sensor is that it functions properly in either air or in liquid. Both resonance frequency and bending modes can be used in liquid. Due to the small mass of MEMS/NEMS devices, they execute thermal motion (Brownian motion) in air and liquid. Therefore, no external excitation technique is needed for exciting cantilevers into resonance.

One surface of the silicon microcantilever can be functionalized so that a given molecular species will be preferentially bound to that surface upon its exposure to a vapor stream. Therefore, detection sensitivity is vastly enhanced by applying an appropriate binding coating on one cantilever surface and an inert coating on the opposite surface thereby enhancing the differential surface stress in the microcantilever. Such an inert coating can, in principle, provide selectivity as well.

The basic requirements for a sensor system are: (i) sensitivity, (ii) selectivity, and (iii) reversibility. While the sensitivity and selectivity are critical, reversibility may be not necessary under some conditions. The lack of selectivity will lead to frequent false positives, which is as bad as false negatives due to lack of sensitivity. However, the degree of selectivity is inherently connected to the reversibility of detection (binding energy, enthalpy).

Selectivity and reversibility (specificity) are often competing characteristics of chemical sensors. The type of interaction occurring between analyte molecules and the cantilever coating determines the adsorption and desorption characteristics. Low-energy, reversible interactions such as physisorption generally lack an acceptable degree of selectivity: the energies involved range from van der Waals interactions (energy ≈0–10 kJ mol⁻¹) to acid-base interactions (energy <40 kJ mol⁻¹). Furthermore, the weak interaction may lead to insufficient sorption, making sensor response weak. At the other end of the spectrum, highly selective (specific) interactions are normally covalent in nature (chemisorption) and are not reversible (binding energies are ≈300 kJ mol$^{-1}$) under normal conditions.

There are two "intermediate-energy" interactions that can be considered to provide limited selectivity while being reversible. One is hydrogen bonding and the other is the formation of coordination complexes. A hydrogen bond is formed by one hydrogen atom and two electronegative atoms, one of which is covalently bound to the hydrogen atom. For example, the O atoms in the characteristic nitro groups of explosives can participate in hydrogen bonding. A coordination complex consists of a central Lewis acid (usually a metal) surrounded by neutral or charged often organic Lewis bases (ligands). In the ligand one or more electron donor atoms interact with the metal ion. The selectivity now can be influenced by the choice of the metal ions as well as by the choice of the ligand, both from an electronic or steric point of view as well as utilizing chelate and surface chelate effects. Previous studies have shown that strongly acidic polymers, such as SXFA-[poly(1-(4-hydroxy-4-trifluoromethyl-5,5,5-trifluoro)pent-1-enyl)methylsiloxane], bind to the basic lone pairs of nitro-groups. The hydrogen bond acidity of the hexafluoroisopropanol group is derived primarily from the strong electron withdrawing nature of the two adjacent trifluoromethyl groups.

In most applications, it is desirable to have the ability to regenerate the sensor, and thus the use of "intermediate range" interactions will be necessary, which in turn broadens the target range. Therefore, normally a single microcantilever coating does not provide sufficient selectivity if reversible sensor operation is required. One exception to this is the detection of hexavalent chromium in a complex matrix using a single cantilever. However, in general, it will be necessary to use an array of microcantilevers with multiple coatings in order to obtain sufficient selectivity especially if the sensor is required to monitor multiple agents. Pattern recognition schemes (using neural analysis) need to be employed to extract the composition of the target vapor stream, especially in the case of mixture.

Much work on coating materials has been done over the years especially in the development of SAW sensors. In this context, various polymer coatings have been investigated. These polymer coatings have been optimized primarily for the use in SAW and QCM sensors where mass loading is the key sensing parameter. This consideration has led to the development of mainly polysiloxane films that allow rapid diffusion of the analyte into the bulk of film to provide optimum mass loading. Self-Assembled Monolayer (SAM) coatings have recently gained attention due to their simplicity and robustness. Some examples of the usage of both polymer and SAM coatings with microcantilever sensors will be presented below.

In recent years many breakthroughs have taken place in the area of microcantilever sensors. Advances in micromachining made it possible to develop arrays of microcantilever beams with required sensitivity. Many chemically selective coatings for chemical speciation have also been developed. Receptor-ligand, antibody-antigen, or enzyme-substrate reactions have been studied for biological detection. Advances also have been made in many other crucial areas such as immobilization of selective agents on cantilever surfaces, and application of selective layers on cantilever arrays. Aided by such tools physical, chemical, and biological detection have been demonstrated using microcantilever sensors. These developments together with the recent advances in neural analysis and telemetry have made possible the development of smart, miniaturized sensors.

The following are specific examples of microcantilever studies relevant to terrorist threat detection.

Bio-warfare agents: While not as prevalent as explosives, the use of chemical/biological agents as a warfare or terrorist weapon is a serious threat. There exist a number of biological agents that can be used as warfare agents. Examples of bio-warfare agents include botulinum toxin, Shiga toxin, diphtheria toxin, anthrax, and ricin, etc. Most of the biological agents are derived from bacterium. Ricin toxin is produced from caster bean extract. Botulinum toxins are some of the most deadly substances known. It is 100,000 times more toxic than nerve agent sarin, and 10,000 times more toxic than VX, and 1000 times more toxic than ricin. The estimated lethal dose of botulinum toxin (type A) is 1 ng/kg of body weight and the lethal blood level of the toxin is around 20 pg/mL. The estimated lethal dose of ricin is 3 μg/kg of body weight. At present there is no widely available rapid test for most biological agents.

We have successfully detected the biowarfare agent ricin using modified microcantilevers. One side of the microcantilever was modified with ricin antibody. When ricin was introduced into a liquid cell housing the cantilever, the cantilever undergoes bending due to ricin-antibody interaction. The experiments were not done under flow conditions. The large response time is due to diffusion of ricin towards the cantilever.

A key requirement for the detection of biological species is the ability to modify the microcantilever surface for biospecific recognition. However, most molecular-recognition-agent-containing molecules are not commercially available, and thus tremendous amounts of synthetic work must be done to develop each molecular-specific microcantilever surface. In this regard, a general microcantilever surface-modification method through layer-by-layer technology for biomolecule recognition was reported. Weeks et al., recently reported the detection of specific *Salmonella enterica* strains using a functionalized microcantilever. Aptamers, essentially specific nucleotides provided by the SELEX® method can be used to detect some infectious agents such as Staphylococcal enterotixin B.

Chemical warfare agents: Basically there are three types of chemical warfare agents: (i) nerve agents, (ii) blister agents, and (iii) irritants. (i) Nerve agents acquired their name because they affect the transmission of nerve impulses in the nervous system by inhibiting acetylcholinesterase. Weaponized nerve agents belong chemically to the group of organo-phosphorus compounds. Examples of nerve agents are GA (tabun), GB (sarin), GD (soman), and VX. (ii) Blister agents burn and blister the skin or any other part of the body they contact. They act on the eyes, mucous membranes, lungs, skin and blood-forming organs. They damage the respiratory tract when inhaled and cause vomiting and diarrhea when ingested. The blister agents include HD (sulphur mustard), HN (nitrogen mustard) and L (Lewisite). (iii) Mucous membrane irritants are chemical agents that attack lung tissue, primarily causing pulmonary edema. In low concentration, irritants act on the respiratory system to cause an accumulation of fluid in the lungs, which can lead to death. In high concentrations, these agents lead to death for the same reason, but might also affect the upper respiratory tract. Chemicals classified as mucous membrane irritants are chloropicrin (PS), chlorine (Cl), phosgene (CG), and diphosgene (DP).

Chemical warfare agents have been used in the past. Nerve agents are among the most toxic of known substances. The nerve agent, either as a gas, an aerosol, or a liquid, enters the body through inhalation or through the skin.

Poisoning may also occur if liquids or foods contaminated with nerve agents are consumed. If a person is exposed to a high concentration of nerve agent, for example, 200 mg sarin/m$^3$, when the agent is absorbed through the respiratory system, death may occur within a couple of minutes.

A self-assembled bilayer of $Cu^{2+}$/L-cysteine on a gold surface has recently been characterized, and recognizes phosphonyl groups due to the formation of strong P=O—$Cu^{2+}$ bonds. We have used a $Cu^{2+}$/L-cysteine bilayer-modified cantilever to detect nerve agents in aqueous solution based on this mechanism. Dimethyl methyl phosphonate (DMMP) was used as a sarin nerve gas simulant. The binding coating of $Cu^{2+}$/L-cysteine bilayer was formed by immersing the cantilever into a $10^{-3}$ M solution of L-cysteine in tris buffer solution (pH=5) for 24 hours. The microcantilever was then rinsed with tris buffer solution and immersed in $10^{-3}$ M $CuSO_4$ tris buffer solution for another 24 hours. When DMMP was introduced into cantilever chamber, the cantilever undergoes bending due to the interaction. When the DMMP is replaced with tris buffer solution, the cantilever does not return to original bending. The flow rate was 4 mL/hour.

It has been shown that phosphonyl groups strongly bind with $Cu^{2+}$ and copper complexes. Organophosphorus compounds are unstable at high pH levels. The cantilever bending due to exposure of DMMP is most likely due to complexation of DMMP with the $Cu^{2+}$/L-cysteine bilayer on the microcantilever surface through $Cu^{2+}$—O=P bonds that alter the surface stress. A cantilever deflection of almost 5 nm can be detected even for a DMMP concentration of $10^{-15}$ M in air. The observed interference from analytes such as sodium phosphate, DL-aspartic acid, dimethylamine, 1,10-phenanthroline, acetic acid and acetonitrile is negligible.

Cantilever Arrays: Although the single cantilever approach seems to work extremely well in laboratory applications, it is less useful in real environment applications where many other parameters can produce signal interference. To avoid this potential problem, it is necessary to look at the differential response of a set, or array, of cantilevers. For example, variations in physical parameters such as temperature, acceleration, and mechanical noises can contribute to cantilever bending. Differential signals obtained by common mode rejection can provide highly sensitive data.

Chemical selectivity can be achieved by arrays consisting of several microcantilevers, each coated with different selective or partially selective coatings. The response of a given modified microcantilever will depend on the concentration of the analyte and the strength of the coating-analyte solubility interactions (e.g. hydrogen bonding, dispersion, and dipole-dipole interactions). A unique response pattern characteristic to a particular analyte can be obtained from an array where each microcantilever is modified with a different coating. The higher the number of modified cantilevers, the greater the uniqueness of the response pattern. Since the microcantilever response to a given analyte depends on the functional end-groups of modifying agents, judicious selection of coatings can lead to significant differences in the response patterns for different analytes. Using an array consisting of a large number of microcantilevers, unique response patterns can be attained for individual analytes, class of analytes, or analytes in complex mixtures. The results of testing with a large number of analyte and mixtures are recorded in a look-up table and referenced routinely when an array is in service.

In order to distinguish target molecules from other species that may be present in the tested gas or liquid stream, an array of cantilevers, each coated with different coating chemically bound to the surface and specifically designed and functionalized to adsorb certain target species (explosives, chemical warfare agents, toxic industrial and other chemicals etc.), can be used. A variety of such coatings have been developed for other types of sensors such as Surface Acoustic Wave sensors and Quartz Crystal Microbalance (QCM). Such coatings can be readily used for the microcantilever sensors and new coatings are being designed and developed. The microcantilever sensors are much more sensitive (especially in the bending mode of operation) compared to the other sensors such as SAW and QCM. A fingerprint pattern recognition approach can be applied in a multiple-cantilever array using a number of cantilevers functionalized with metals, metal oxides, organic SAMs and polymeric coatings (specific only for certain classes of compounds), which respond with a specific pattern of different signal characteristics to a given target species or a mixture of target species. Upon calibration, the intensity of given pattern is related to the concentration of certain target species in a complex mixture, as illustrated for other types of chemical sensors. For example: 1) Gold and other noble metal coatings are specific for organic thiols, dialkyl sulfides and disulfides, including sulfur mustard gas and HT (blister warfare agents); 2) Platinum cantilever coatings and $Cu^{2+}$-modified SAMs bind strong ligands like ammonia (toxic industrial chemical), toxic organic amines, blood agents (cyanogen chloride, hydrogen cyanide, etc.); 3) Pyridine and amino-terminated coatings, upon protonation, can detect acids produced by spontaneous hydrolysis of phosgene (a chocking warfare agent), hydrogen chloride (toxic industrial chemical) and others. Pyridine-functionalized cantilevers in acidic aqueous solutions are also extremely sensitive for toxic chromate ions; 4) Chlorine gas (chocking agent and toxic industrial chemical) may be detected by sacrificial reactive metal coatings like Fe, Cu, etc; 5) Other chemicals can be detected using inorganic coatings (such as titanium, titanium oxides, aluminum oxide, other metals, and metal oxides etc.), that can be selected from well-known heterogeneous catalytical reactions. An example would be adsorption of acetylene, benzene, or other unsaturated hydrocarbons on palladium; 6) Nerve agent detection using cantilevers has been described in publication; Y. M. Yang, H. F. Ji, T. Thundat, "Nerve agents detection using a $Cu^{2+}$/L-cysteine bilayer-coated microcantilever", Journal of the American Chemical Society, 125 (2003) 1124, herein incorporated by reference; 7) Using hydrosilylation procedure, which in certain cases can be combined with sequential surface reactions, it is possible to derive coatings containing various molecular recognition groups such as hydrocarbon chains, esters, metal-containing organic functionalities, buckyballs (C-60), and even hydroxyls. One example is the use of hydrocarbon layers grafted directly on the silicon surface for gasoline detection; 8) For the detection of biological species specific interactions between dendrimer biocides and bacterial membranes can be used. In addition, similar interactions can be achieved by creating suitable mixed self-assembled monolayers, oligomers and polymers, thus optimizing the surface stress on the cantilever.

The following patents and publications, all herein incorporated by reference, further describe structure and coatings used with the microcantilevers of this invention;

1. E. A. Wachter and T. G. Thundat, "Microbar Sensor", U.S. Pat. No. 5,445,008.
2. E. Houser and R. McGill, "Chemoselective Dendrimeric Compounds for Use in Chemical Sensors", U.S. Pat. No. 6,617,040.

3. L. A. Pinnaduwage et al., *Applied Physics Letters* 83 (2003) 1471.
4. R. M. Crooks and A. J. Ricco, *Accounts in Chemical Research* 31 (1998) 219.
5. C. Z. Chen and S. L. Cooper, Biomaterials 23 (2002) 3359.
6. K. J. Albert et al., *Chem. Rev.* 100 (2000) 2595.
7. L. A. Pinnaduwage et al., *Sensor Letters* 2 (2004) 25.
8. Y. M. Yang, H. F. Ji, T. Thundat, "Nerve agents detection using a Cu2+/L-cysteine bilayer-coated microcantilever", *Journal of the American Chemical Society*, 125 (2003) 1124.
9. J. M. Buriak, "Organometalic Chemistry on silicon and germanium surfaces", *Chemical Reviews*, 102 (2002) 1271.
10. S. Edmondson et al., *Chem. Soc. Rev.* 33 (2004) 14.
11. S. D. Jayasena, "Aptamers: An emerging class of molecules that rival antibodies in diagnosis", *Clinical Chemistry*, vol. 45, pp. 1628–1650 (1999).
12. K. Yano and I. Karube, "Molecularly imprinted polymers for biosensor applications", *Trends in Analytical Chemistry*, vol. 18, pp. 199–204 (1999).
13. V. I. Boiadjiev, G. M. Brown, L. A. Pinnaduwage, G. Goretzki, P. V. Bonnesen, and T. Thundat, "Photochemical Hydrosilylation of 11-Undecenyltriethylammonium Bromide with Hydrogen-Terminated Si Surfaces for the Development of Robust Microcantilever Sensors for Cr(VI)", *Langmuir*, ASAP Article 10.1021/la047852n S0743-7463(04)07852-7; Web Release Date: Jan. 20, 2005.
14. D. Mandler, I. Turyan, "Determination of Chromium", U.S. Pat. No. 6,090,269.

Sensitivity Enhancement with Pre-Concentration: Detection speed is a challenging issue especially for chemical, biological, and radiological exposures. For instance, a few seconds may be all the time available to respond to threat-level quantities of a nerve agent. Especially with the slower reaction rates of biological agents, detection times of seconds to minutes could limit the amount inhaled and simplify subsequent prophylactic action.

Even though the enhanced sensitivity of microcantilevers is due primarily to their small size (i.e., the large surface-to-volume ratio which greatly amplifies the bending signal), the small size also decreases the probability of target molecules being captured onto the sensor surface. This loss could be compensated by using a pre-concentration system at the front end of the microcantilever sensor. Pre-concentrators that can rapidly bring a sufficient quantity of agent into the detection volume of the cantilever element are essential for significantly decreasing the detection time. Preconcentrators collect analyte from a large volume of air and then release the collected sample in a small amount of air. Typically, a packing is used for adsorption of the analyte which is desorbed, typically by heat.

The collection of airborne or surface-attached samples of chemical, biological, and radiological agents could be a key component of a total detection system. Employing pre-concentrators based on nanostructures is very attractive. A pre-concentrator (front-end collection system) must match the flow impedance of the detection sensor for the system to be fully functional. The most efficient collection systems would employ some type of pre-concentration column with uncoated or specifically coated nanoparticles for increased surface area. The pre-existing macro-scale pre-concentrators such as those used for industrial hygiene and environmental air sampling can be used in situations where miniaturization is not necessary.

Signal Transduction and Transmission: When making a miniature sensor, it is not enough just to have a small sensor element. Signal transduction and transmission capabilities also need to be incorporated into a small package. Here we will briefly discuss the current status of these two important components.

Since the advent of the AFM, several signal transduction methods have been explored for monitoring microcantilever deflections. These include optical, piezoresistive, piezoelectric, and capacitive methods. In the optical method, a laser diode is focused at the free-end of a cantilever. The reflected light is detected with a position-sensitive detector (PSD). In the piezoresistive method, the silicon cantilever is doped with boron to half of its thickness. The electrical resistance of the boron channel changes as a function of cantilever bending. In piezoelectric method, cantilever bending causes a transient charge on a piezoelectric film, such as ZnO, on the cantilever. Because the signal is transient it is not ideal for static cantilever-bending measurements. In the capacitive method, the capacitance between the cantilever, which is micromachined with a space between the cantilever and the substrate, is measured.

From the studies conducted over the past decade by a large number of research groups it appears that piezoresistive method, initially developed by Tortonese et al, is the best solution so far for making an integrated, small-scale sensor. Even though the optical detection could be somewhat superior in sensitivity, it involves alignment of a laser beam and thus is not convenient or particularly robust. Recently, Boisen et al., reported a piezoresistive readout that is optimized for measuring microcantilever surface stress. Using this method, Cantion, Inc. (Denmark) has developed a commercial system (C-Box) that can be used to measure the piezoresistive cantilever-bending stress. Using a Cantion C-Box, we have measured the bending response of a piezoresistive microcantilever coated with the 4-mercaptobenzoic SAM coating. FIG. 4 shows a data set on microcantilever response to an RDX stream of 290-ppt concentration.

Sensor arrays are broad spectrum detectors useful in security operations at transportation hubs, public and private building and on a battlefield. Environmental sampling and process control are non-security areas wherein the arrays offer advantages of size, simplicity and reliability.

INDUSTRIAL UTILITY

The modified microcantilevers of this invention can be used as portable sensors for screening busses, trucks, aircraft and buildings and for the detection of hazardous materials passing through airports, train stations, bus stations, ports and building entrances.

The invention has been described in terms of specific embodiments which are indicative of a broad utility but are not limitations to the scope of the invention. Additions and modifications apparent to those with skill in the art are included within the scope and spirit of the invention.

We claim:
1. Functionalized cantilevers comprising:
   at least one cantilever having a top surface, bottom surface, and mounted on a base;
   a binding coating of self-assembled monolayers further comprising 4-MBA; said binding coating formed on said at least one cantilever which exhibits a binding interaction with at least one agent selected from the group consisting of RDX and PETN; and a means for detecting bending and resonant frequency changes of said at least one cantilever resulting from said binding interaction.

2. Functionalized cantilevers according to claim 1 wherein said binding interaction causes a change in surface stress in the cantilever.

3. Functionalized cantilevers according to claim 1 wherein said binding interaction is reversible.

4. Functionalized cantilevers according to claim 1 wherein said metallic binding coating further comprises a metal selected from at least one of the group consisting of Au, Pt, Cu, Pd, Ti, Al and their oxides.

5. Functionalized cantilevers according to claim 1 wherein said means for detecting further comprises at least one method selected from the group consisting of optical, piezoresistive, piezoelectric, and capacitive.

6. Functionalized cantilevers according to claim 1 wherein said cantilevers are disposed in an array.

* * * * *